(12) United States Patent
Kharas

(10) Patent No.: US 9,146,220 B2
(45) Date of Patent: Sep. 29, 2015

(54) COBALT-MOLYBDENUM SULFIDE CATALYST MATERIALS AND METHODS FOR STABLE ALCOHOL PRODUCTION FROM SYNGAS

(71) Applicant: ALBEMARLE CORPORATION, Baton Rouge, LA (US)

(72) Inventor: Karl Kharas, Louisville, CO (US)

(73) Assignee: ALBEMARLE CORPORATION, Baton Rouge, LA (US)

(*) Notice: Subject to any disclaimer, the term of this patent is extended or adjusted under 35 U.S.C. 154(b) by 14 days.

(21) Appl. No.: 14/056,375

(22) Filed: Oct. 17, 2013

(65) Prior Publication Data

US 2014/0045269 A1 Feb. 13, 2014

Related U.S. Application Data

(60) Division of application No. 12/769,850, filed on Apr. 29, 2010, now Pat. No. 8,586,801, which is a continuation-in-part of application No. 12/204,543, filed on Sep. 4, 2008, now Pat. No. 7,923,405.

(60) Provisional application No. 61/174,528, filed on May 1, 2009.

(51) Int. Cl.
*G01N 31/10* (2006.01)
*B01J 23/85* (2006.01)
(Continued)

(52) U.S. Cl.
CPC ............... *G01N 31/10* (2013.01); *B01J 23/85* (2013.01); *B01J 23/882* (2013.01); *B01J 27/049* (2013.01); *B01J 27/0515* (2013.01); *B01J 37/03* (2013.01); *B01J 37/20* (2013.01);

*C07C 29/156* (2013.01); *C01B 2203/025* (2013.01); *C01B 2203/0233* (2013.01); *C01B 2203/0283* (2013.01)

(58) Field of Classification Search
CPC ...................................................... B01J 37/00
See application file for complete search history.

(56) References Cited

U.S. PATENT DOCUMENTS 2,094,128 A 9/1937 Lazier et al.
2,629,729 A 2/1953 Layng
(Continued)

FOREIGN PATENT DOCUMENTS

WO 2008048364 4/2008

OTHER PUBLICATIONS

Yurchak, S., et al., Process Aging Studies in the Conversin of Methanol to Gasoline ina Fixed Bed Reactor, 1979, Ind. Eng. Chem. Process Des. Dev., vol. 18, No. 3, pp. 527-534.*

(Continued)

*Primary Examiner* — Yate K Cutliff
(74) *Attorney, Agent, or Firm* — Nathan C. Dunn; James A. Jubinsky; Marcy M. Hoefling

(57) ABSTRACT

The present invention provides methods and compositions for the chemical conversion of syngas to alcohols. The invention includes catalyst compositions, methods of making the catalysts, and methods of using the catalysts including techniques to maintain catalyst stability. Certain embodiments teach compositions for catalyzing the conversion of syngas into products comprising at least one $C_1$-$C_4$ alcohol, such as ethanol. These compositions generally include cobalt, molybdenum, and sulfur, and avoid metal carbides both initially and during reactor operation.

13 Claims, 4 Drawing Sheets

(51) Int. Cl.

| | |
|---|---|
| *B01J 23/882* | (2006.01) |
| *B01J 27/049* | (2006.01) |
| *B01J 27/051* | (2006.01) |
| *B01J 37/03* | (2006.01) |
| *B01J 37/20* | (2006.01) |
| *C07C 29/156* | (2006.01) |

(56) References Cited

U.S. PATENT DOCUMENTS

| | | | |
|---|---|---|---|
| 2,755,257 | A | 7/1956 | Donovan et al. |
| 2,767,202 | A | 10/1956 | Rottig |
| 4,623,634 | A | 11/1986 | Sapienza et al. |
| 4,675,344 | A | 6/1987 | Conway et al. |
| 4,752,622 | A | 6/1988 | Stevens |
| 4,752,623 | A | 6/1988 | Stevens et al. |
| 4,831,060 | A | 5/1989 | Stevens et al. |
| 4,882,360 | A | 11/1989 | Stevens |
| 5,010,049 | A | 4/1991 | Villa-Garcia et al. |
| 6,063,633 | A * | 5/2000 | Willson, III .............. 436/37 |
| 6,331,574 | B1 | 12/2001 | Lapidus et al. |
| 6,586,254 | B1 * | 7/2003 | Kumar et al. .............. 436/7 |
| 6,617,464 | B2 | 9/2003 | Manzer |
| 6,921,733 | B2 | 7/2005 | Mahajan |
| 7,041,621 | B2 | 5/2006 | Ramani |
| 7,923,405 | B2 | 4/2011 | Kharas et al. |
| 2003/0059356 | A1 * | 3/2003 | Hoke et al. .............. 423/210 |
| 2010/0076228 | A1 | 3/2010 | Alsum et al. |
| 2010/0152498 | A1 | 6/2010 | Kharas et al. |
| 2010/0210741 | A1 | 8/2010 | Kharas |
| 2010/0280287 | A1 | 11/2010 | Kharas et al. |

OTHER PUBLICATIONS

W. P. Dianis, "Characterization of Metal Sulfide Fischer-Tropsch Catalysts by Temperature Programmed Desorption", Applied Catalysis 30 (1987) 99-121.

Pio Forzatti et al, "Higher Alcohol Synthesis", Catalysis Reviews, 33:1, 109-168 (Feb. 1, 1991).

Jamshid Iranmahboob and Donald O. Hill, "Alcohol Synthesis From Syngas Over K2CP3/CoS/MoS2 on Activated Carbon", Catalysis Letters, vol. 78, Nos. 1-4, pp. 49-55 (Mar. 2002).

C.B. Murchison et al, Mixed Alcohols From Syngas Over Moly Catalysts, Proc. 9th Intern. Cong. Catal., vol. 2, pp. 626-633 (1988).

C.B. Murchison et al, "Mixed Alcohols From Syngas Over Moly Catalysts", Proc. 9th Intern. Cong. Catal., vol. 5, pp. 256-259 (1988).

Craig B. Murchison, DOE Higher Alcohol Workshop, "Syngas + Methanol to Higher Alcohols Over (CoS).5MoS2 Catalysts" (Oct. 26, 1993).

S. Phillips et al, "Thermochemical Ethanol via Indirect Gasification and Mixed Alcohol Synthesis of Lignocellulosic Biomass", NREL Technical Report/TP-510-41168 (Apr. 2007).

Roger Ruan, "Challenges and Opportunities for Biomass Refining", University of Minnesota (Sep. 2007).

I. Simakova et al, "Complex Mediums VI: Light and Complexity", edited by Martin W. McCall et al, Proceedings of SPIE, vol. 5924, 592413-1 through 592413-7 (2005).

C.H. Chang et al, "Infrared and Raman Studies of Amorphous MoS3 and Poorly Crystalline MoS2", Journal of Catalysis, vol. 72, pp. 139-148 (1981).

H. W. Wang et al, "Synthesis of Molybdenum Disulphide by Acidification of Ammonium Tetrathiomolybdate Solutions", Journal of Materials Science Letters, vol. 15, No. 6, pp. 494-496 (Jan. 1996).

* cited by examiner

COBALT-MOLYBDENUM SULFIDE CATALYST MATERIALS AND METHODS FOR STABLE ALCOHOL PRODUCTION FROM SYNGAS

PRIORITY DATA

This patent application is a continuation-in-part of U.S. patent application Ser. No. 12/204,543 for "COBALT-MOLYBDENUM SULFIDE CATALYST MATERIALS AND METHODS FOR ETHANOL PRODUCTION FROM SYNGAS," filed Sep. 4, 2008. This patent application also claims priority to U.S. Provisional Patent Application No. 61/174,528 for "COBALT-MOLYBDENUM SULFIDE CATALYST MATERIALS AND METHODS FOR STABLE ALCOHOL PRODUCTION FROM SYNGAS," filed May 1, 2009. Each of these patent applications is incorporated by reference herein for all purposes.

FIELD OF THE INVENTION

The present invention generally relates to the field of catalysts for the chemical conversion of synthesis gas to alcohols. The invention relates to catalyst compositions, methods of making catalysts, methods of using catalysts, methods of maintaining catalytic activity, and methods of characterizing catalysts.

BACKGROUND OF THE INVENTION

Synthesis gas (hereinafter referred to as syngas) is a mixture of hydrogen ($H_2$) and carbon monoxide (CO). Syngas can be produced, in principle, from virtually any feedstock material containing carbon. Carbonaceous materials commonly include fossil resources such as natural gas, petroleum, coal, and lignite. Renewable resources such as lignocellulosic biomass and various carbon-rich waste materials can also be used to produce syngas. It is preferable to utilize a renewable resource to produce syngas because of the rising economic, environmental, and social costs associated with fossil resources.

There exist a variety of conversion technologies to turn these various feedstocks into syngas. Conversion approaches can utilize a combination of one or more steps comprising gasification, pyrolysis, steam reforming, and/or partial oxidation of a carbon-containing feedstock.

Syngas is a platform intermediate in the chemical and biorefining industries and has a vast number of uses. Syngas can be converted into alkanes, olefins, oxygenates, and alcohols. These chemicals can be blended into, or used directly as, diesel fuel, gasoline, and other liquid fuels. Syngas can also be directly combusted to produce heat and power.

U.S. Pat. No. 4,752,623 (Stevens and Conway) discloses a catalyst for producing mixed alcohols from syngas, wherein the catalyst contains either molybdenum or tungsten, in addition to either cobalt or nickel, both components being in sulfided form. Stevens and Conway emphasize that it is not necessary for their invention that any particular stoichiometric metal sulfide be present. Sulfided cobalt is often assigned to CoS in the literature. Further, Stevens and Conway state that no advantage is realized by the presence of sulfur in the feed.

U.S. Pat. No. 4,675,344 (Conway et al.) describes a method for controlling the ratio of methanol to higher alcohols by adjusting the concentration of a sulfur-releasing compound in the feed to a reactor containing alkali-promoted $MoS_2$ catalysts. Conway teaches that such catalysts should exclude Group VIII elements, such as cobalt, to realize the selectivity benefit of sulfur addition.

Murchison et al. discuss the use of cobalt-molybdenum sulfides for mixed-alcohol synthesis in volumes 2 (pages 626-633) and 5 (pages 256-259) of the *Proceedings of the 9th International Congress on Catalysis* (1988). Murchison stated that cobalt (or nickel) molybdenum sulfide materials could be operated without added $H_2S$. On page 257, Murchison stated that "[t]he effect of $H_2S$ in increasing the chain length of the alcohols is very specific for the alkalinized moly sulfide, both supported and unsupported. The addition of cobalt to the catalyst results in higher molecular weight alcohols without $H_2S$ addition and makes the catalyst selectivity substantially independent of the $H_2S$ of the feed . . . " During the discussion at the 9th International Congress on Catalysis, as recorded at page 258, a questioner commented that "Santiestaban et al. indicate carbides are not formed" and poses a question, in response to which Murchison stated "[t]here is certainly no problem in long term stability without $H_2S$ if one is not concerned with maximizing $C_{2+}$ alcohols. The XRD and XPS work we have done has not shown any carbide formation for the sulfided catalysts." Murchison teaches that Co/Mo sulfides will be stable for alcohol synthesis in the absence of $H_2S$ and that carbides do not form as the catalyst acquires operating time on stream.

The existing art provides little, if any, information concerning chemical or physical characteristics that tend to correlate with the performance of cobalt-molybdenum-sulfide alcohol-synthesis catalysts, including Co—Mo—S, and similar catalyst systems comprising Ni and/or W. Particularly absent is information relating to preferred amounts of sulfur, on a stoichiometric basis, relative to other major components present.

Furthermore, the existing art does not provide guidance with respect to maintain catalytic stability (in sulfided systems) for long periods of time. Yet, catalyst lifetime and stability (i.e., the maintenance of activity and selectivity) are critical from a commercial point of view, for economic reasons.

In light of these shortcomings in the art, what are needed are methods of making preferred sulfided catalyst compositions, methods of using these catalyst compositions, and methods of maintaining sufficient activity and sulfide content to convert syngas into alcohols, such as ethanol.

SUMMARY OF THE INVENTION

In some variations, this invention provides methods of producing at least one $C_1$-$C_4$ alcohol from syngas, the method comprising:

(a) providing a reactor including a catalyst composition comprising cobalt, molybdenum, and sulfur, wherein at least some of the cobalt and some of the sulfur are present as a cobalt-sulfur association having a molar ratio of sulfur to cobalt (S:Co), calculated by assuming all molybdenum is present as $MoS_2$;

(b) flowing syngas into the reactor at conditions effective to produce at least one $C_1$-$C_4$ alcohol; and (c) injecting additional sulfur, or a compound containing sulfur, into the reactor in an amount that is sufficient to maintain at least some of the cobalt in a sulfided state, and is further sufficient to maintain the molybdenum in a completely sulfided state.

The additional sulfur injected can be contained in one or more compounds selected from the group consisting of elemental sulfur, hydrogen sulfide, dimethyl sulfide, diethyl sulfide, dimethyl disulfide, any isomers of dibutyl polysulfide (such as ditertbutyl polysulfide), any isomers of dioctyl polysulfide, diphenyl polysulfide, dicyclohexyl polysulfide, methylthiol, ethylthiol, cysteine, cystine, methionine, potassium disulfide, cesium disulfide, and sodium disulfide.

In some variations, this invention provides a method for maintaining catalyst stability while producing at least one $C_1$-$C_4$ alcohol from syngas, the method comprising:

(a) providing a reactor including a catalyst composition comprising cobalt, molybdenum, and sulfur;

(b) flowing syngas into the reactor at conditions effective to produce at least one $C_1$-$C_4$ alcohol; and (c) injecting additional sulfur, or a compound containing sulfur, into the reactor, in an amount that is sufficient to inhibit the formation of cobalt carbides or molybdenum carbides under the conditions effective to produce at least one $C_1$-$C_4$ alcohol.

In preferred embodiments, step (c) inhibits the formation of cobalt carbides, such as crystalline $Co_2C$. In preferred embodiments, step (c) inhibits the formation of molybdenum carbides. In some embodiments, step (c) prevents any formation of cobalt carbides or molybdenum carbides. The additional sulfur provided in step (c) can maintain at least some of the cobalt in a sulfided state. Also, the additional sulfur can maintains the molybdenum in a sulfided state.

In some embodiments, the method includes maintaining, for at least 1000 hours, preferably at least 5000 hours, and more preferably at least 10,000 hours on-stream, one or more parameters selected from the group consisting of CO conversion, ethanol selectivity, total alcohol selectivity, total alcohol productivity, and methane selectivity.

Certain embodiments include an additional step of recovering sulfur downstream of the reactor and recycling at least a portion of the sulfur into the reactor.

Other variations of the present invention provide a method of accelerated aging of a sulfided catalyst for the conversion of syngas to alcohols, the method comprising:

(a) providing a test reactor including a test catalyst containing sulfur;

(b) flowing syngas into the test reactor at conditions effective to produce an alcohol; and (c) injecting a suitable aging accelerant into the test reactor, wherein the aging accelerant is capable of causing sulfur loss from the test catalyst at a rate that is faster than the rate in the absence of the aging accelerant.

The aging accelerant can be methanol, or any other suitable chemical that causes sulfur loss. Methanol is preferred, in some embodiments. The methanol can be injected in step (c) at about the equilibrium amount in accordance with the methanol/syngas reaction equilibrium under the conditions in step (b).

The accelerated-aging method can be conducted for a test time selected from about 1-200 hours, such as about 10-100 hours. The acceleration factor should be greater than unity and can be, in various embodiments, at least 5, 10, 20, or more.

The accelerated-aging method preferably includes measuring at least one parameter of interest at a plurality of times during operation of the test reactor, to generate a test response. The parameter of interest can be selected from the group consisting of CO conversion, ethanol selectivity, total alcohol selectivity, total alcohol productivity, methane selectivity, and sulfur concentration exiting the test reactor. Other parameters can be used, as well.

In some embodiments, the test response includes at least one correlation selected from the group consisting of decreasing CO conversion, decreasing ethanol selectivity, decreasing total alcohol selectivity, decreasing total alcohol productivity, increasing methane selectivity, and increasing sulfur concentration exiting the test reactor. Some embodiments further include characterizing the test catalyst by predicting the lifetime or stability of a commercial catalyst with substantially the same composition as the test catalyst.

Some variations provide a method of characterizing a plurality of sulfided catalysts, wherein each catalyst composition is a distinct catalyst that is independently subjected to the following steps:

(a) providing a test reactor suitable for evaluating each of the sulfided catalysts;

(b) for each of the sulfided catalysts, flowing syngas into the test reactor at conditions effective to produce an alcohol; and (c) for each of the sulfided catalysts, injecting a suitable aging accelerant into the test reactor, wherein the aging accelerant is capable of causing sulfur loss from each of the sulfided catalysts at a rate that is faster than the rate in the absence of the aging accelerant.

Some variations provide a method of characterizing performance of a sulfided catalyst for the conversion of syngas to alcohols under a plurality of process conditions, the method comprising:

(a) providing a test reactor suitable for evaluating the sulfided catalyst;

(b) for each of the plurality of process conditions, flowing syngas into the test reactor at conditions effective to produce an alcohol; and (c) for each of the plurality of process conditions, injecting a suitable aging accelerant into the test reactor, wherein the aging accelerant is capable of causing sulfur loss from each of the sulfided catalysts at a rate that is faster than the rate in the absence of the aging accelerant.

DETAILED DESCRIPTION OF EMBODIMENTS OF THE INVENTION

Figure 1:
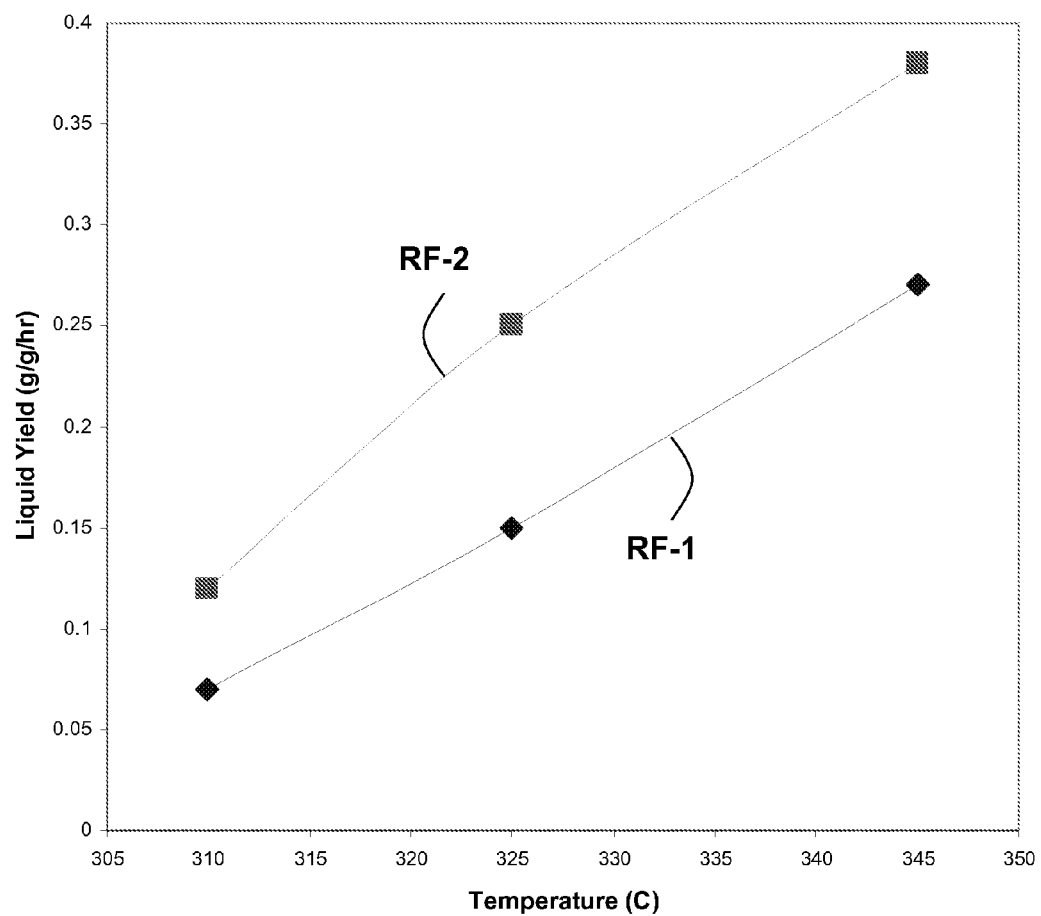
FIG. 1 is a graph depicting the effect of catalyst type and reactor temperature on experimental total-liquids yield.

This description will enable one skilled in the art to make and use the invention, and it describes several embodiments, adaptations, variations, alternatives, and uses of the invention, including what is presently believed to be the best mode of carrying out the invention. As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon the specific analytical technique. Any numerical value inherently contains certain errors necessarily resulting from the standard deviation found in its respective testing measurements.

The present invention will now be described by reference to the following detailed description, which characterizes some preferred embodiments but is by no means limiting.

For present purposes, "catalyst composition" means a composition of a catalytic material that is not activated. An "activated catalyst composition" is a composition of a catalytic material that is suitably activated (or regenerated). By "activated" it is meant that the catalyst is exposed to conditions (such as, but not necessarily, reactor conditions) that render it more suitable for its intended purpose, which in this case means the conversion of syngas to alcohols.

Base promoters can enhance the production of alcohols from syngas. By "base promoter" it is meant one or more metals that promote the production of alcohols. Base promoters may be present in free or combined form. The base promoter can be present as a metal, oxide, carbonate, hydroxide, sulfide, as a salt, in a compound with another component, or some combination of the above.

It has been discovered that preferred variants of catalyst compositions for converting syngas to alcohols (e.g., $C_1$-$C_4$ alcohols) comprise cobalt-molybdenum-sulfide powders which have certain characteristic chemical signatures. These preferred catalyst compositions are relatively rich in sulfur. Specifically, the amount of sulfur present in preferred catalysts is higher than would be expected by a skilled artisan, based on typical oxidation numbers of cobalt and molybdenum in sulfide compounds.

In some embodiments, the amount of sulfur present is in excess of that expected if cobalt occurs as $CoS_2$ and molybdenum occurs as $MoS_2$. In some preferred embodiments, the amount of sulfur present is in excess of that expected if cobalt occurs as $Co_3S_4$ and molybdenum occurs as $MoS_2$, as will be described in more detail below and in Examples 1 and 2.

Additionally, preferred compositions of cobalt-molybdenum-sulfide alcohol-synthesis catalysts are relatively unreactive toward gentle leaching into non-oxidizing aqueous mineral acids, such as hydrochloric acid. Furthermore, preferred variants of cobalt-molybdenum-sulfide catalysts are slightly more reactive toward sulfur leaching into solvents such as chloroform, as compared to less-preferred catalyst compositions.

As used herein, chloroform leaching of elemental sulfur refers to an analytical extraction of the sulfur into substantially pure chloroform ($CHCl_3$), conducted at a temperature selected from about 20° C. to about 55° C. or higher, and preferably at about 55° C. As is known, a variety of solvents are capable of extracting elemental sulfur into solution. It is preferable, but not critical, that chloroform is used. Other solvents that can be effective include toluene, methylene chloride, xylenes, benzene, acetone, carbon tetrachloride, and carbon disulfide. Some compositions of the present invention will be described in terms of chloroform leaching, and it will be appreciated that similar results can be obtained by leaching into other solvents effective for elemental sulfur.

As used herein, hydrochloric acid leaching of a metal refers to an analytical extraction of the metal into a solution of 3N HCl, conducted at room temperature (such as about 25° C.) or at higher temperature (such as about 90° C.). Other acids can be effective. Generally, a moderately strong, non-oxidizing mineral acid is preferred. For example, dilute solutions of one or more acids selected from HBr, HI, $HBF_4$, or $HPF_6$ can be used. Preferably, acid concentrations for the leaching tests are low enough to avoid possible total digestion of the material.

In HCl, which is preferred, an additional role of chloride is thought to stabilize oxospecies of molybdenum in the leachate with respect to reprecipitation. It is noted that a metal may be leached in non-elemental forms, such as aqueous cations or aqueous salts.

In some embodiments of Co—Mo—S catalyst compositions provided by the present invention, sulfur is present in a total (free or combined form) amount of at least 40 wt % of the catalyst composition. In some preferred embodiments, total sulfur is between 42-44 wt % of the composition.

Preferred compositions do not contain very much elemental sulfur (typically regarded as $S_8$); i.e., they are not a mere physical mixture of sulfur with the other elements present. A non-zero amount of elemental sulfur can be present in preferred compositions. Namely, favored sulfided catalysts include elemental sulfur in an amount of at least about 100 ppm, calculated on a total-catalyst weight basis. The concentration of elemental sulfur is preferably between about 150-5000 ppm, more preferably between about 300-1000 ppm. Amounts higher than 5000 ppm of elemental sulfur can be effective from a catalysis standpoint, but there are practical concerns. For example, high levels of elemental sulfur in the compositions can melt and/or sublime in the catalyst bed, leading to operational problems. High levels of elemental sulfur could also lead to undesired formation of hydrogen sulfide or carbonyl sulfide.

The amount of elemental sulfur present in preferred catalysts can also be related to convenient chloroform leaching tests as described above. In certain embodiments, at least about 0.02% (but preferably not more than about 0.1%) of the total sulfur present is capable of leaching into chloroform. It is preferable that at least about 0.05% of the sulfur be capable of leaching into chloroform.

Preferred catalyst compositions for converting syngas into alcohols are highly sulfided, with cobalt associated with sulfide. In some embodiments, dispersed and crystalline $CoS_2$ is present in these catalysts. It is known that high-valency transition metals can oxidize sulfur to disulfide ($S_2^{2-}$) or even polysulfide species, with associated reduction at the metal center. Polysulfides are anions with the general formula $S_n^{2-}$ (n>2) and the general structure $^-SS_{n-2}S^-$.

The molar ratio of sulfur to cobalt ("S:Co"), given an initial assignment of sulfur to molybdenum to yield $MoS_2$, is regarded as an important parameter. As used herein, S:Co is calculated after assigning some of the sulfur to molybdenum by assuming all molybdenum is present in the catalyst composition as $MoS_2$. The S:Co molar ratio can optionally be calculated after subtracting sulfur that is capable of leaching into chloroform (or a similarly effective solvent), which will tend to account for elemental sulfur. The S:Co molar ratio can also optionally be calculated after subtracting sulfur that is capable of leaching into 3 N HCl (or a similarly effective dilute acid), which will tend to account for sulfur in the form of sulfates, sulfites, persulfates, hyposulfites, and the like. In some embodiments, the S:Co molar ratio can be calculated to account for all forms of sulfur that are soluble in (i.e., capable of leaching into) both chloroform and 3 N HCl. Preferred compositions do not have excessive amounts of these forms of sulfur, so the calculated S:Co molar ratios are typically not especially sensitive to the exclusion of sulfur species that are soluble in chloroform and/or 3 N HCl.

The S:Co molar ratio in the cobalt-sulfur association is at least about 1.2. Preferably, the molar ratio S:Co is at least about 1.5, and more preferably at least about 2.0. In some embodiments, S:Co is between about 2.0 and about 4.0. For example, for illustration purposes only, various specific embodiments of the invention can employ S:Co ratios of about 1.2, 1.3, 1.35 (i.e., slightly higher than what would be expected if cobalt were present as $Co_3S_4$), 1.4, 1.5, 1.75, 1.95, or 2.0. Various other specific embodiments can use S:Co ratios of about 2.05, 2.1, 2.2, 2.3, 2.4, 2.5, 2.6, 2.7, 2.8, 2.9, or 3.0. In other embodiments, S:Co ratios can exceed 3.0, such as up to and including about 4.0 or higher. These higher S:Co ratios can occur, for instance, when polysulfide anions are associated with cobalt.

In some embodiments of Co—Mo—S catalyst compositions, cobalt is present in an amount between about 3-21 wt %, preferably between about 10-16 wt %, and more preferably between about 13-15 wt % (wherein wt % is weight percent based on the total catalyst composition). In some embodiments of Co—Mo—S catalyst compositions, molybdenum is present in an amount between about 33-56 wt %, preferably between about 35-50 wt %, and more preferably between about 40-45 wt %.

In preferred embodiments, the molar ratio of molybdenum to cobalt, Mo:Co, can generally be between about 1 and about 20, preferably between about 1.5 and about 8, and more preferably about 2.

The mass fraction of total sulfur (i.e. sulfur in free or combined form) is preferably greater than 40 wt % for catalyst compositions when the Mo:Co mole ratio is about 2. Alcohol-synthesis catalysts can, however, use Mo:Co mole ratios different from 2, as described above. As the Mo:Co mole ratio varies, the desirable mass fraction of sulfur will also preferably vary. In preferred embodiments, the catalyst composition includes sufficient sulfur so that all Mo can occur as $MoS_2$, with additional sulfur so as to maintain cobalt in a sulfided state.

It is preferable that the catalyst composition includes sulfur in an oxidation state that is relatively high, for the sulfur in association with cobalt. In some embodiments, the average oxidation number for sulfur in association with cobalt is greater than −2, preferably at least about −1.5, and more preferably about −1. Average sulfur oxidation states can be in the range of −2 to −1 or higher, according to the present invention, for the sulfur in association with cobalt.

In $Co_3S_4$, wherein S:Co=1.33, the oxidation number of cobalt is both +2 and +3 (formally $Co_3S_4$ is $[Co(II)][Co(III)]_2S_4$). The average oxidation state of sulfur in $Co_3S_4$ is −2. In $CoS_2$, wherein S:Co=2, the oxidation number of cobalt is +2 and the sulfur oxidation number is −1. Cobalt-sulfur associations having higher S:Co molar ratios are expected to have higher (less negative) sulfur oxidation numbers. In light of the preferred S:Co molar ratios as described above, preferred embodiments of the catalyst compositions of the invention will include at least a portion of sulfur in the −1 oxidation state.

The amount and nature of cobalt present in preferred catalysts can be related to convenient hydrochloric acid leaching tests as described above. In some embodiments, less than about 8% of the total cobalt present is capable of leaching into a 3N HCl solution. It is preferable that less than about 5%, 3%, 2%, 1%, or less (including substantially none) of the total cobalt is capable of leaching into 3N HCl. "Substantially none" means that no metal is measured by standard detection techniques, but a small amount may in fact be present in the 3N HCl leachate.

The amount and nature of molybdenum present in preferred catalysts can be related as well to these convenient hydrochloric acid leaching tests. In some embodiments, less than about 1.0% of the total molybdenum present is capable of leaching into a 3N HCl solution. It is preferable that less than about 0.5%, 0.3%, 0.2%, 0.1%, or less (including substantially none) of the total molybdenum is capable of leaching into 3N HCl.

Other aspects of the invention relate to preferred sulfide stoichiometries pertaining to nickel-molybdenum-sulfide, cobalt-tungsten-sulfide, and nickel-tungsten-sulfide catalyst compositions. When Ni is employed rather than Co, the amount of sulfur present will be in excess of that which would be expected if Mo occurs as $MoS_2$ and Ni as NiS. When tungsten is used rather than molybdenum, the amount of sulfur present will be in excess of that which would occur if cobalt were present as CoS, or nickel as NiS, and tungsten present as $WS_2$.

Some embodiments of the present invention provide a catalyst composition for catalyzing the conversion of syngas into alcohols, the composition comprising sulfur, a first element or plurality of elements E1 and a second element or plurality of elements E2, wherein: E1 is cobalt and/or nickel; E2 is molybdenum and/or tungsten; at least some of E1 and some of the sulfur are present as an E1-sulfur association; and the molar ratio of sulfur to E1 (S:E1) in the association is at least 1.2, the molar ratio S:E1 calculated after assigning some of the sulfur to E2 by assuming all E2 is present in the composition as $E2S_2$, and optionally after subtracting any sulfur that is soluble in chloroform and/or 3 N HCl. In certain embodiments, the molar ratio S:E1 is at least 1.5, preferably between about 2.0 and about 4.0, selected in a similar manner as described above for S:Co.

E1 can be present in an amount between about 2 wt % and about 25 wt %, and E2 can be present in an amount between about 25 wt % and about 95 wt % of the composition. In some embodiments, E1 is present in an amount between about 10-25 wt % of the composition, and E2 is present in an amount between about 25-60 wt %.

In some embodiments, total sulfur is present in a total amount of at least 30 wt % of the composition. This total sulfur preferably includes at least 100 ppm elemental sulfur. In certain preferred embodiments, at least 0.02% of the sulfur is capable of leaching into chloroform at 25° C. In preferred embodiments, less than about 5% of E1 and less than about 0.5% of E2 is capable of leaching into a 3N HCl solution at 25° C.

Generally, preferred Ni—Mo—S, Co—W—S, or Ni—W—S catalysts will be similarly resistant toward leaching metals into gentle mineral acid, as are preferred Co—Mo—S catalysts. As will be appreciated by a skilled artisan, similar methods can be recited for catalysts containing complex mixtures, such as Co—Ni—Mo—W—S catalysts.

Aspects of the present invention also relate to methods of making these catalyst compositions. The catalytic species may be dispersed by methods known in the art. Examples include impregnation from solution followed by conversion to the sulfided species or intimate physical mixing. One or more of these methods may be used. It is preferred that at least two of the catalytic components (i) Mo and/or W, (ii) Co and/or Ni, and (iii) S are intimately mixed. More preferably, all of these catalyst components are substantially intimately mixed.

In some embodiments, the catalyst composition further includes at least one base promoter which can increase selectivities to alcohols from syngas. In some embodiments, at least one base promoter includes one or more elements selected from the group consisting of potassium, rubidium, cesium, barium, strontium, scandium, yttrium, lanthanum, or cerium, in free or combined form.

The base promoter is preferably at least present at a level sufficient to render the catalyst more basic. The base promoter is generally present in an amount of at least about 0.01 wt %, with metal promoters calculated as if a free element in the catalyst. Preferably, the base promoter is present in an amount of at least 0.1 wt %, more preferably between about 1 wt % and 20 wt %.

The base promoter may be added as an ingredient to a catalytic component or to a support, or may be part of one of the catalytic components or as an integral part of the support. The base promoter may be added to the active catalytic element prior to, during, or after the formation of the sulfide. For example, physical mixing or solution impregnation may be employed.

In certain embodiments of the present invention, ammonium tetrathiomolybdate can by made by addition of ammonium sulfide solution or hydrogen sulfide gas to a solution of a soluble molybdate, such as (for example) ammonium heptamolybdate. To this solution, cobalt acetate solution may be added to provide a suspension wherein the Mo:Co ratio is about 2. Without being limited by any particular theory, it is presently believed that these embodiments take advantage of the insolubility of the $[NH_4^+]_2[Mo_2CoS_8^{2-}]$ salt.

If Mo:Co mole ratios different from two are desired, some $[NH_4^+]_2[Mo_2CoS_8^{2-}]$ salt still forms. When cobalt is in excess, it may coprecipitate by assuring an excess of sulfide anion is present at the time of cobalt precipitation, resulting in an intimately mixed precipitate. This precipitate comprises an amorphous cobalt sulfide and $[NH_4^+]_2[Mo_2CoS_8^{2-}]$ salt. If Mo is desired to be present in excess of Mo:Co=2:1, its precipitation may be favored by controlling the temperature of coprecipitation at a temperature lower than about 50° C. Solubility of ammonium tetrathiomolybdate is rather strongly temperature dependent, decreasing at lower temperatures. Nickel and tungsten react with very similar trends.

To the $[NH_4^+]_2[Mo_2CoS_8^{2-}]$ precipitate, an aqueous solution of, for example, an acetate salt of a lanthanide-series metal or of barium or strontium may be added by incipient-wetness impregnation. The composition is then calcined under inert conditions, in certain embodiments. "Inert conditions" with respect to calcining means that (i) the atmosphere at the inlet to the calciner (or other apparatus effective for calcining Co—Mo—S materials) is substantially free of $O_2$ and $H_2O$, and further that (ii) separation of $H_2O$ and volatile components (such as $NH_3$, $S_8$, and the like) from the solid catalyst phase is efficient. $N_2$ and Ar, if suitably free of contaminating water and oxygen, represent suitable carrier gases for the calcinations.

Alternately, the ammonium cobalt thiomolybdate may be calcined under inert conditions prior to addition of the base promoter. In this case, it is typically convenient to grind, under a substantially inert atmosphere, a salt (e.g., an acetate or carbonate salt) of a base promoter such as potassium or cesium.

The catalyst can take the form of a powder, pellets, granules, beads, extrudates, and so on. When a catalyst support is optionally employed, the support may assume any physical form such as pellets, spheres, monolithic channels, etc. The supports may be coprecipitated with active metal species; or the support may be treated with the catalytic metal species and then used as is or formed into the aforementioned shapes; or the support may be formed into the aforementioned shapes and then treated with the catalytic species.

In embodiments of the invention that employ a catalyst support, the support is preferably (but not necessarily) a carbon-rich material with large mesopore volume, and further is preferably highly attrition-resistant. One carbon support that can be utilized is "Sibunit" activated carbon (Boreskov Inst. of Catalysis, Novosibirsk, Russia) which has high surface area as well as chemical inertness both in acidic and basic media (Simakova et al., Proceedings of SPIE—Volume 5924, 592413, 2005). An example of Sibunit carbon as a catalyst support can be found in U.S. Pat. No. 6,617,464 (Manzer).

The present invention also relates to use of catalyst compositions. In some embodiments of the invention, a reactor is loaded with a catalyst comprising a composition as described herein. A process stream comprising syngas is fed into the reactor at conditions effective for producing alcohols from the syngas.

In some embodiments, conditions effective for producing alcohols from syngas include a feed hydrogen/carbon monoxide molar ratio ($H_2/CO$) from about 0.2-4.0, preferably about 0.5-2.0, and more preferably about 0.5-1.5. These ratios are indicative of certain embodiments and are not limiting. It is possible to operate at feed $H_2/CO$ ratios less than 0.2 as well as greater than 4, including 5, 10, or even higher. It is well-known that high $H_2/CO$ ratios can be obtained with extensive steam reforming and/or water-gas shift in operations prior to the syngas-to-alcohol reactor.

In embodiments wherein $H_2/CO$ ratios close to 1:1 are desired for alcohol synthesis, partial oxidation of the carbonaceous feedstock can be utilized. In the absence of other reactions, partial oxidation tends to produce $H_2/CO$ ratios close to unity, depending on the stoichiometry of the feedstock.

When, as in certain embodiments, relatively low $H_2/CO$ ratios are desired, the reverse water-gas shift reaction ($H_2+CO_2 \rightarrow H_2O+CO$) can potentially be utilized to consume hydrogen and thus lower $H_2/CO$. In some embodiments, $CO_2$ produced during alcohol synthesis or elsewhere, can be recycled to the reformer to decrease the $H_2/CO$ ratio entering the alcohol-synthesis reactor. Other chemistry and separation approaches can be taken to adjust the $H_2/CO$ ratios prior to converting syngas to alcohols, as will be appreciated. For example, certain commercial membrane systems are known to be capable of selectively separating $H_2$ from syngas, thereby lowering the $H_2/CO$ ratio.

In some embodiments, conditions effective for producing alcohols from syngas include reactor temperatures from about 200-400° C., preferably about 250-350° C.; and reactor pressures from about 20-500 atm, preferably about 50-200 atm or higher. Generally, productivity increases with increasing reactor pressure. Temperatures and pressures outside of these ranges can be employed.

In some embodiments, conditions effective for producing alcohols from syngas include average reactor residence times from about 0.1-10 seconds, preferably about 0.5-2 seconds. "Average reactor residence time" is the mean of the residence-time distribution of the reactor contents under actual operating conditions. Catalyst space times or catalyst contact times can also be calculated by a skilled artisan and these times will typically also be in the range of 0.1-10 seconds, although it will be appreciated that it is certainly possible to operate at shorter or longer times.

In general, the specific selection of catalyst configuration (geometry), $H_2/CO$ ratio, temperature, pressure, residence time (or feed rate), and other reactor-engineering parameters will be selected to provide an economical process. These parameters are not regarded as critical to the present invention. It is within the ordinary skill in the art to experiment with different reactor conditions to optimize selectivity to a particular product or some other parameter.

Product selectivities can be calculated on a carbon-atom basis. "Carbon-atom selectivity" means the ratio of the moles of a specific product to the total moles of all products, scaled by the number of carbon atoms in the species. This definition accounts for the mole-number change due to reaction. The selectivity $S_j$ to general product species $C_{xj}H_{yj}O_{zj}$ is $$S_j = \frac{x_j F_j}{\sum_i x_i F_i}$$

wherein $F_j$ is the molar flow rate of species j which contains $x_j$ carbon atoms. The summation is over all carbon-containing species ($C_{xi}H_{yi}O_{zi}$) produced in the reaction.

In some embodiments, wherein all products are identified and measured, the individual product selectivities sum to unity (plus or minus analytical error). In other embodiments, wherein one or more products are not identified in the exit stream, the selectivities can be calculated based on what products are in fact identified, or instead based on the conversion of reactants. In the latter case, the selectivities may not sum to unity if there is some mass imbalance. Nevertheless, this method can be preferable as it tends to determine more accurate selectivities to identified products when it is suspected that at least one reaction product is not measured.

"$CO_2$-free carbon-atom selectivity" or "$CO_2$-free selectivity" mean the percent of carbon in a specific product with respect to the total carbon converted from carbon monoxide to some product other than carbon dioxide. It is the same equation above for $S_j$, except that $i \neq CO_2$ and $j \neq CO_2$.

In various embodiments of the present invention, the product stream from the reactor may be characterized by $CO_2$-free selectivities of about 10-40% to methanol and about 20-60% or higher to ethanol. In some preferred embodiments, the ethanol $CO_2$-free selectivity is higher, preferably substantially higher, than the methanol $CO_2$-free selectivity, such as a $CO_2$-free selectivity ratio of ethanol/methanol in the product of about 1.0, 1.5, 2.0, 2.5, 3.0, or higher. The product stream can also contain more methanol than ethanol, on either a mole basis or a carbon-atom basis, in certain embodiments. The $CO_2$-free selectivity ratio of ethanol to all other alcohols is preferably at least 1, more preferably at least 2.

The product stream from the reactor may include up to about 25% $CO_2$-free selectivity to $C_{3+}$ alcohols, and up to about 10% to other non-alcohol oxygenates such as aldehydes, esters, carboxylic acids, and ketones. These other oxygenates can include, for example, acetone, 2-butanone, methyl acetate, ethyl acetate, methyl formate, ethyl formate, acetic acid, propanoic acid, and butyric acid.

Another aspect of the invention relates to methods for activating, or otherwise generating, preferred activated catalyst compositions. In some embodiments, an activated catalyst composition is prepared by first providing a starting catalyst composition comprising cobalt, molybdenum, and sulfur, wherein at least some of the cobalt and some of the sulfur are present as a cobalt-sulfur association, and wherein the molar ratio of sulfur to cobalt (S:Co) in the association is at least 1.2, the molar ratio S:Co calculated by assuming all molybdenum is present in the catalyst composition as $MoS_2$. This starting catalyst composition is then subjected to a stream of syngas under suitable activation conditions, preferably in situ within the reactor, such that the S:Co molar ratio (calculated in the same way as for the starting catalyst composition) decreases to a ratio that is at least somewhat lower than the S:Co molar ratio in the starting catalyst composition. In various embodiments, the S:Co molar ratio decreases to about 1.5, 1.4, 1.3, 1.2, 1.1, 1.0, 0.9, 0.8, 0.7, 0.6, 0.5, 0.4, 0.3, 0.2, 0.1, or even less, provided at least some of the cobalt remains in a sulfided state.

In certain embodiments of this aspect relating to catalyst activation, with reference to the above-described hydrochloric acid leaching tests, a first amount of total cobalt contained in the starting catalyst composition is capable of leaching into a 3N HCl solution, and a second amount of total cobalt contained in the activated catalyst composition is capable of leaching into a 3N HCl solution. Preferably, the second amount of cobalt is greater than the first amount of cobalt that can leach. For example, when less than about 5% of the total cobalt present in the starting catalyst composition can leach into a 3N HCl solution, more than about 5% of the total cobalt present in the activated catalyst composition can leach into a 3N HCl solution. When less than about 1% of the total cobalt in the non-activated catalyst composition can leach into a 3N HCl solution, more than about 1% of the total cobalt in the activated catalyst composition can leach into such a solution.

During activation, the catalyst can become more reduced, with evolution of various light sulfur compounds such as $H_2S$, $CH_3SH$, $CH_3SCH_3$, $CH_3CH_2SH$, and the like. In some variations, it can be beneficial (but is by no means necessary) to add sulfide back to the activated or operating catalyst composition to compensate for the sulfur that evolves during activation or operation. Yet another aspect of the present invention provides methods to maintain certain sulfide levels in the activated catalyst compositions. In these methods, sulfur or a compound containing sulfur can be injected into the reactor, in an amount that is sufficient to maintain both the cobalt and the molybdenum in sulfided states.

In some embodiments of this aspect, additional sulfur is injected so as to control the molar ratio S:Co to between about 1.2 to about 2 or higher, up to about 4. Catalyst samples can be analyzed to measure S:Co and, if needed, additional sulfur can be introduced. Alternately, experiments can be separately conducted to establish that additional sulfur is necessary at certain times, or as a continuous injection in prescribed amounts, or some other program, in order to control (maintain) the S:Co ratio. S:Co is "measured and controlled" within the meaning herein whether the measurements are made prior to, or during, reactor operation.

In some embodiments, additional sulfur can be introduced by injecting, in dissolved form or another effective form, one or more compounds selected from elemental sulfur, hydrogen sulfide, dimethyl sulfide, diethyl sulfide, dimethyl disulfide, any isomers of dibutyl polysulfide (such as ditertbutyl polysulfide), any isomers of dioctyl polysulfide, diphenyl polysulfide, dicyclohexyl polysulfide, methylthiol, ethylthiol, cysteine, cystine, methionine, potassium disulfide, cesium disulfide, and/or sodium disulfide. Various isomers of these compounds may be used. For example, cysteine may be present as L-cysteine, D-cysteine, or D,L-cysteine mixtures. This list of potential sulfur-containing compounds is merely exemplary and by no means limits the scope of the invention.

For the purpose of adding to the reactor, one or more of these sulfur-containing compounds can be dissolved in, for example, toluene or other organic solvents. For the disulfides of potassium, sodium, or cesium, effective solvents may be selected from alcohols, short-chain polyethylene glycols, acetonitrile, DMF, DMSO, or THF, for example.

Here, "injecting" sulfur can mean feeding sulfur into the reactor at the entrance, or introducing sulfur into the catalyst bed in any other way. Injecting includes introduction of sulfur as part of a syngas feed stream that comprises sulfur. Injecting can also include shutting down the normal operation of the reactor (syngas to alcohols) and then flowing a sulfur-containing compound through the catalyst bed in some fashion, to cause a change in the S:Co ratio.

Some variations of the present invention are premised on the discovery that extended operation of an alkali-promoted Co/Mo/S catalyst, in the absence of co-fed hydrogen sulfide, leads to substantial loss of sulfur from the catalyst. Furthermore, it has been realized that extended catalyst operation results in a substantial fraction of Co and Mo occurring as non-crystalline carbides, according to elemental analysis. For example, after 1000 hours or more on stream, the formation of crystalline $Co_2C$ is readily observed by XRD.

Carbide formation in Co/Mo/S catalysts, whether the metal carbide is crystalline or non-crystalline, is not favorable and should be avoided when alcohols are desired products. Cobalt carbide and/or molybdenum carbide tend to reduce CO conversion, reduce ethanol selectivity, reduce total alcohol selectivity, and increase methane selectivity, at the same process conditions suitable for ethanol synthesis from syngas when carbides are not present.

In order to operate a stable alcohol-synthesis process for a commercially reasonable amount of time, such as in excess of 1000 hours, the presence of a sulfiding agent in the feed, or in another stream into the reactor, is very beneficial. A sulfiding agent is desired to operate for an extended period of time without formation of less active and less selective transition-metal carbides. Also, a sulfiding agent is beneficial to operate for an extended period of time without deterioration of ethanol selectivity or formation rates (ethanol productivity).

In some embodiments, alkali-promoted Co/Mo/S catalysts require ongoing sulfur feeding and optionally sulfur recycle. For example, $H_2S$ or another suitable sulfur-releasing compound could be introduced with syngas fed to the reactor. Dimethyl disulfide (DMDS) is preferred, in some embodiments. It is expected that DMDS will convert, in the presence of $H_2$, to $H_2S$ and $CH_4$ over alkali-promoted Co/Mo/S catalysts. The $H_2S$ generated in-situ can help maintain sulfide levels in the catalysts.

In some embodiments, sulfur compounds result in the product, and a portion or all of these sulfur compounds can be recycled to an upstream part of the process, such as into the alcohol-synthesis reactor. This mode of operation can reduce costs associated with fresh sulfiding agents as well as minimize sulfur disposal costs.

Some carbonaceous feedstocks that can produce syngas (for use in the present invention) also contain sulfur. In some embodiments, sulfur compounds can be recovered from the selected feedstock upstream of the alcohol-synthesis reactor, and these sulfur compounds can be used as sulfiding agents. For example, sulfur compounds could be generated during devolatilization, extracted during syngas clean-up or conditioning, and so on.

Catalyst lifetime is an economically significant parameter. While there are various reasons why a sulfided catalyst "ages" and loses stability, it will be recognized by a skilled artisan that sulfur loss is a critical component in catalyst lifetime. But it is not practical to test every potential catalyst in long-term reactor operation. It therefore would be desirable to establish a technique wherein catalyst aging can be accelerated in a meaningful way. Certain variations of the present invention provide methods of "accelerated aging," that is, characterizing or predicting catalyst stability over extended periods of operation—without actually operating reactors for extended periods.

In some embodiments, co-feeding syngas with methanol accelerates the rate of sulfur loss. Sulfur loss can lead to carbide formation as described herein, but these variations should not be limited by any particular theory or hypothesis, or by any specific fate of insufficiently sulfided metals.

Process conditions for accelerated aging can vary widely. The invention is not limited to particular conditions but rather is intended to predict stability across ranges of conditions. Exemplary conditions for accelerated aging of a Co/Mo/S/K catalyst are as follows: $H_2/CO=2$, 325° C., GHSV of 8500/hr, 1500 psig, recycle ratio=4, and a methanol injection rate of about 25 mol/kg-cat/hr. The methanol injection rate can vary from, for example, about 1-100 mol/kg-cat/hr, such as about 10-50 mol/kg-cat/hr, in some embodiments. In certain embodiments, the amount of methanol injected is about the equilibrium amount (according to the methanol/syngas reaction equilibrium) at or near the entrance to the catalytic reactor.

The amount of time necessary to establish a prediction of long-term stability can vary, depending on conditions employed and the nature of the catalyst being tested. The amount of time can also be a function of the desired degree of accuracy (e.g., rough screening versus detailed predictions for scale-up). In some embodiments, the test time can be selected from about 1 hour to about 200 hours, e.g. about 10-100 hours. It can be preferable to test at constant conditions for at least about 50 hours to detect aging. The minimum testing time should be that period of time capable of detecting a statistically significant loss in catalyst activity.

An important outcome of accelerated-aging tests is the "acceleration factor," which means the enhancement in aging rate realized during accelerated aging by the methods described herein, compared to the aging rate that would result from actual extended operation. The acceleration factor is calculated as the rate of sulfur loss from a test catalyst in the presence of an aging accelerant divided by the rate of sulfur loss in the absence of the aging accelerant. This factor should at least be unity to realize a benefit. In various embodiments, the acceleration factor can be at least about 2, 3, 4, 5, 8, 10, 15, 20, 25, 50, 75, 100 or more.

An accelerated-aging test need not actually run for a length of time given by the predicted catalyst lifetime divided by the acceleration factor. The testing time can actually be shorter. To illustrate, a test conducted for 50 hours with an acceleration factor of 20 would be capable of explicitly characterizing catalyst performance up until 1000 hours under real conditions. Provided there is some detectable loss in stability over this period of time, and a satisfactory correlation can be established, performance can be predicted for periods well in excess of 1000 hours—such as 2,000, 5,000, 10,000 hours or more.

Many types of predictions can be used. For example, a threshold ethanol selectivity could be chosen, wherein the predicted catalyst lifetime is the period of time up until the ethanol selectivity falls below the threshold. It is noted that exact correlations are not necessary, provided there are trends during accelerated aging that can be utilized to predict ultimate catalyst performance.

Methanol injection is useful as an aging accelerant in Co/Mo/S catalyst systems, but methanol is by no means the only species that can be employed for this purpose. Any hydrocarbon, oxygenate, organic acid, or other functional group that is capable of removing sulfur from sulfided metals can be employed. It will be recognized that different aging accelerants will have different efficiencies of sulfur removal and may cause other surface reactions that could serve to otherwise alter the catalyst stability. A person of ordinary skill in the art can select an aging accelerant and conduct initial experiments to establish relevant correlations, such as is demonstrated in Example 7.

Accelerating aging can be beneficial to characterize multiple catalyst compositions in an effort to screen for commercially desirable materials. Accelerating aging can also be beneficial to examine different process conditions, to understand the impact on catalyst aging and lifetime. Finally, accelerating aging can be useful to prescribe a quantity of sulfur to be injected to maintain stability.

In some commercial embodiments, the levels of sulfur may need to vary over time. Accelerated again could allow one to establish a dynamic profile of sulfur addition over the lifetime of a catalyst. To illustrate, sulfur levels in the feed to a catalyst undergoing accelerated aging could be adjusted systematically until catalyst stability changes, thereby indicating an amount of sulfur compounds to employ at various times.

EXAMPLES

Example 1

Performance of Compositions RF-1 and RF-2

Two catalyst compositions are produced and given the designations RF-1 and RF-2. Both compositions generally comprise Co—Mo—S and are produced in a similar manner, according to the description herein above, but the ultimate compositions that are obtained are different. The synthesis of RF-2 employs conditions that tend to exclude the atmosphere to a greater extent than the conditions for synthesis of RF-1.

In separate experiments, RF-1 and RF-2 catalysts are loaded into a reactor and tested for their capability to convert syngas into liquid products including ethanol. In these experiments, the primary variables are catalyst type (RF-1 or RF-2) and reactor temperature (310° C., 325° C., or 345° C.). A full-factorial experimental design is carried out, with 2×3=6 experiments. These experiments are each controlled to 30% CO conversion by adjusting space velocities.

Figure 2:
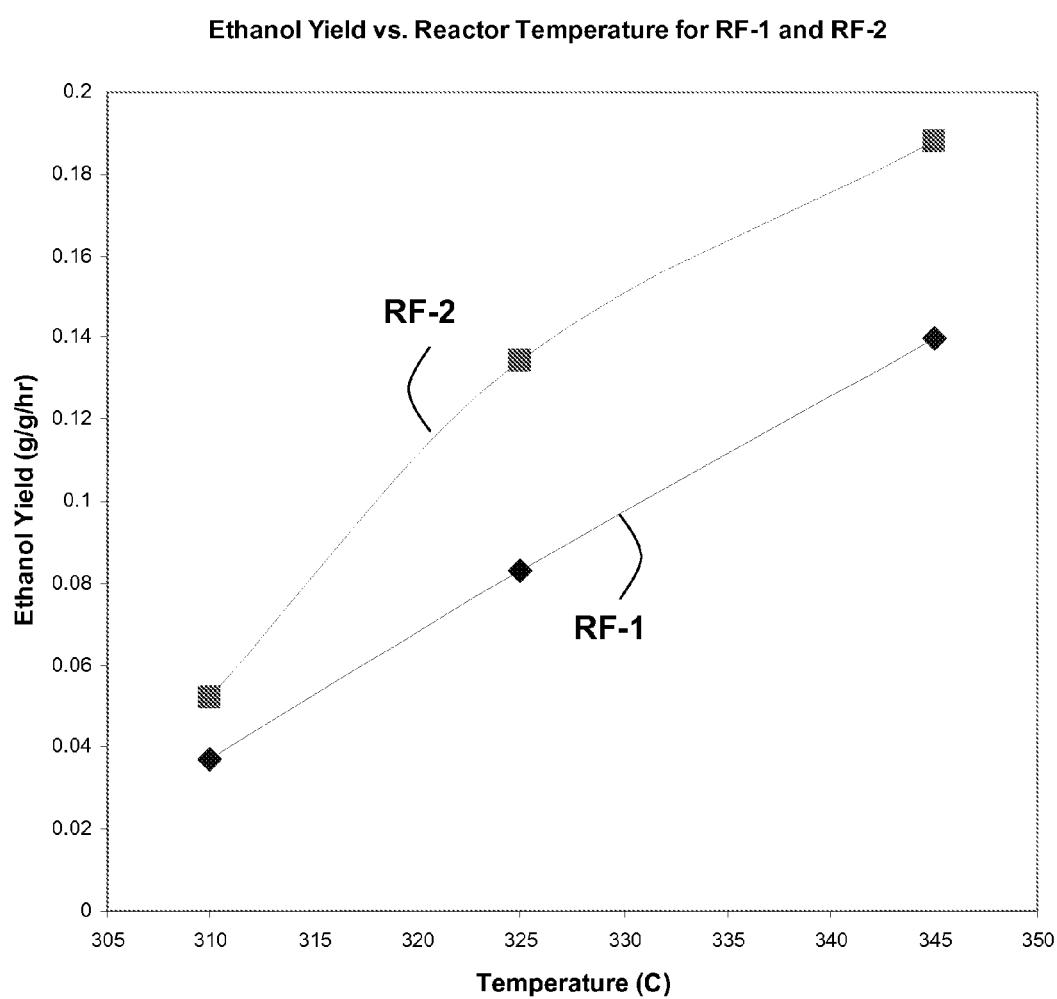
FIG. 2 is a graph depicting the effect of catalyst type and reactor temperature on experimental ethanol yield.

FIG. 1 shows the impact of catalyst and temperature on total liquid yield. FIG. 2 depicts the ethanol yield versus temperature, calculated as grams of liquid product per gram of catalyst per hour, for the two different catalysts RF-1 and RF-2. Also analyzed (not shown) are other alcohols including methanol, propanol, and butanol; water; and organic acids. From FIG. 2, it is experimentally observed that RF-2 is the superior catalyst of the two at any of the temperatures tested.

Example 2

Characterization of Compositions RF-1 and RF-2

The two catalyst compositions tested in actual reactors in Example 1, referred to as RF-1 and RF-2, are characterized in this example. The analysis for both compositions includes LECO S analysis, to determine total sulfur content; leaching the materials with chloroform, to assess the amount of elemental sulfur present; and leaching with 3N HCl, to assess the amount of hydrophilic, soluble sulfur, cobalt, and molybdenum. Three separate samples for each composition RF-1 and RF-2 are analyzed.

The mass fractions of total cobalt and total molybdenum are essentially the same for both RF-1 and RF-2, while the mass fractions of total sulfur are different (see tables below). The wt % numbers indicate the mean±standard deviation of the measurements. A t test value greater than 0.05 implies that there is no statistical basis to assert that differences exist, for that particular parameter, between RF-1 and RF-2.

|  | Total Co (wt %) | Total Mo (wt %) | Total S (wt %) |
| --- | --- | --- | --- |
| RF-1 | 14.43 ± 0.84 | 44.8 ± 2.2 | 38.70 ± 0.80 |
| RF-2 | 13.67 ± 0.48 | 42.0 ± 2.4 | 42.71 ± 0.44 |
| t test | 0.09 | 0.07 | $6.1 \times 10^{-6}$ |

The amount of elemental sulfur (chloroform-leachable sulfur) is higher in RF-2 than in RF-1, as shown below. RF-2 is slightly more reactive toward leaching of elemental sulfur than RF-1. This result is consistent with a more highly sulfided, less hydrophilic or oxophilic material for catalyst composition RF-2.

|  | Elemental Sulfur (wt %) |
| --- | --- |
| RF-1 | 0.0088 ± 0.0031 |
| RF-2 | 0.0382 ± 0.0045 |
| t test | $4.3 \times 10^{-7}$ |

More cobalt and molybdenum from RF-1 leach into 3N HCl solution than from RF-2. The amounts of sulfur that leach into 3N HCl are comparable for the two materials.

| Leachable Material into 3 Normal HCl Aqueous Solutions | | | |
| --- | --- | --- | --- |
|  | wt % Leachable S | wt % Leachable Co | wt % Leachable Mo |
| RF-1 | 0.365 ± 0.074 | 1.49 ± 0.18 | 1.08 ± 0.17 |
| RF-2 | 0.432 ± 0.023 | 0.402 ± 0.042 | 0.125 ± 0.15 |
| t test | 0.08 | $1.1 \times 10^{-5}$ | $3.2 \times 10^{-5}$ |

RF-2 is relatively non-reactive toward metal leaching by 3N HCl. Given the assumption that Mo is present as $MoS_2$, as described above, a molar S:Co ratio can be calculated and the degree of sulfidation can be assessed.

|  | S:Co Mole Ratio |
| --- | --- |
| RF-1 | 1.13 ± 0.27 |
| RF-2 | 1.97 ± 0.25 |
| t test | $2.3 \times 10^{-4}$ |

Given the results of Example 1 (e.g., FIG. 2) in conjunction with the characterizations in Example 2, preferential aspects of compositions for higher-alcohol synthesis catalysts are revealed.

Example 3

Experimental Co:S Molar Ratios for Certain Preferred Catalyst Compositions of the Invention In this example, 18 distinct Co—Mo—S catalysts are synthesized in a manner experimentally similar to the procedure to synthesize RF-2 in Example 1. Due to imperfect process control, some variations in composition arise. A representative reactor experiment at 325° C. and 30% CO conversion (for reasons explained in Example 1) gives a liquid yield of about 0.21 g/g/hr and an ethanol yield of about 0.1 g ethanol per g catalyst per hour. With reference to the performance of RF-1 and RF-2, as shown in FIGS. 1 and 2, the performance of this single catalyst was measurably better than RF-1.

All 18 lots of catalyst in this example are analyzed by the same techniques as described in Example 2. It is of interest to consider the S:Co molar ratio, given an initial assignment of sulfur to molybdenum to yield $MoS_2$.

Figure 3:
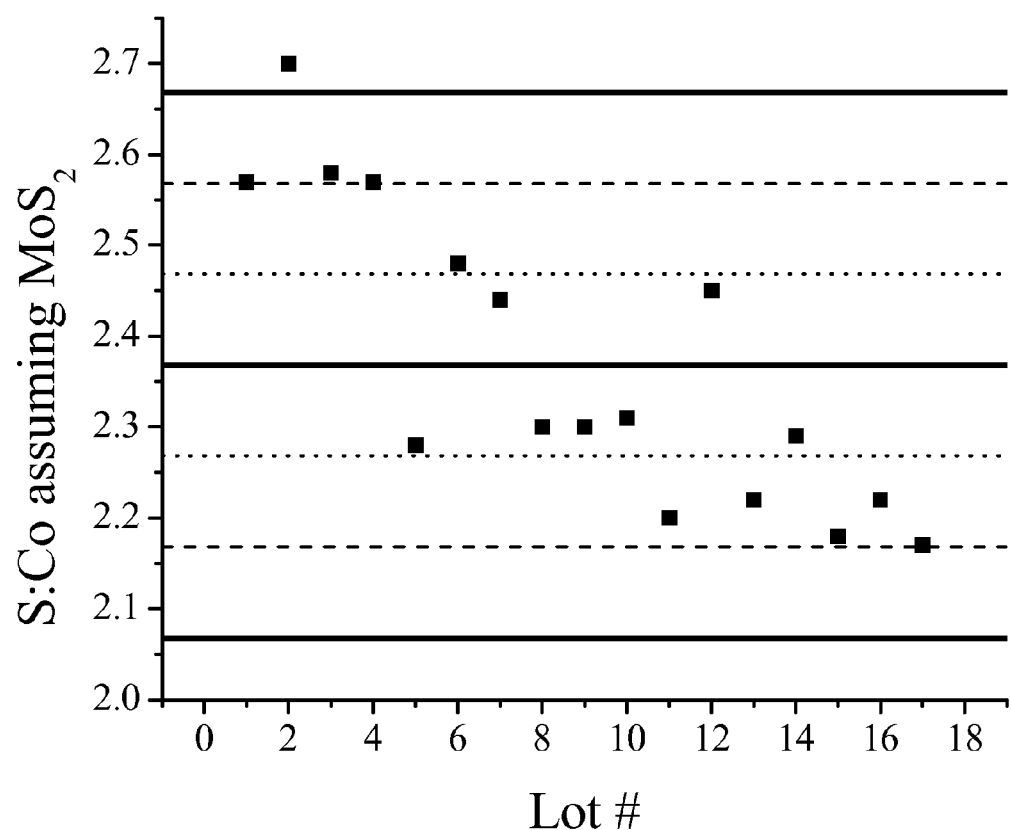
FIG. 3 is a chart showing S:Co molar ratios associated with certain preferred catalyst compositions.

FIG. 3 depicts the S:Co molar ratios across the 18 lots of catalysts synthesized in this example, wherein S:Co is calculated after subtracting elemental sulfur as determined by leaching into chloroform at room temperature. This ratio varies between about 2.2 and about 2.7, with an average of about 2.4.

Figure 4:
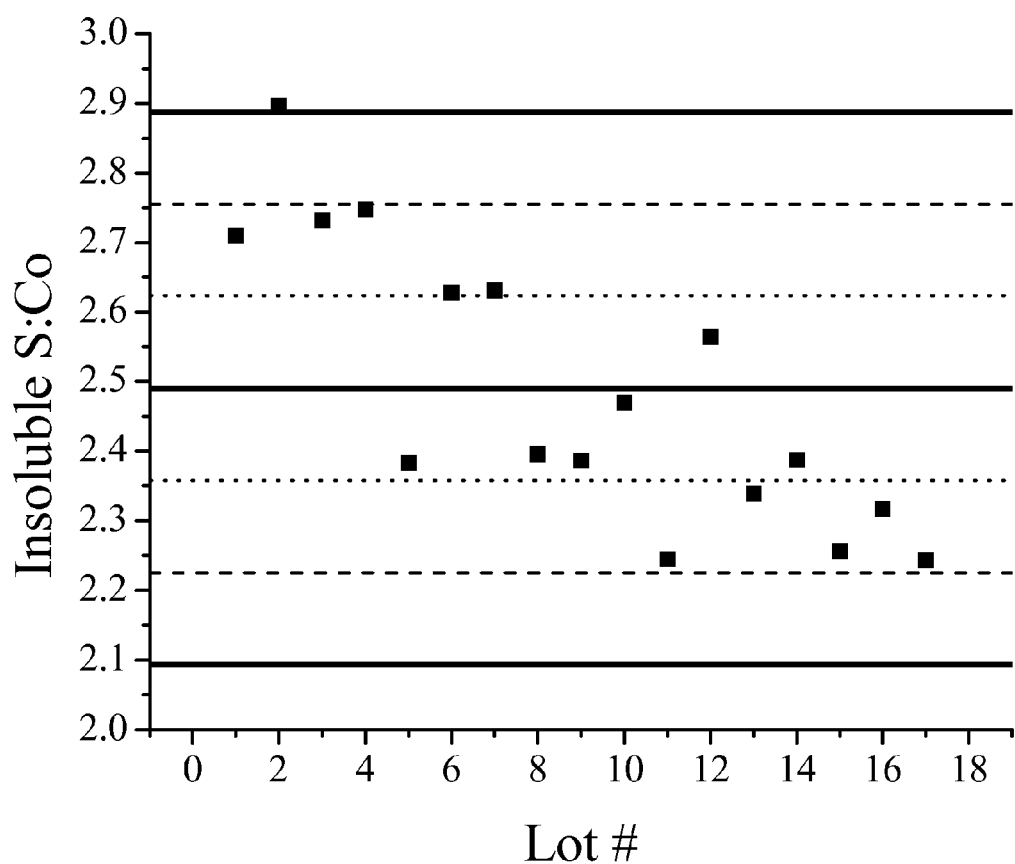
FIG. 4 is a chart showing S:Co molar ratios associated with certain preferred catalyst compositions.

FIG. 4 shows the S:Co molar ratios across the 18 lots of catalysts, wherein S:Co here subtracts the sulfur species (presumably primarily sulfate) soluble in 3 N HCl, as well as the sulfur that is soluble in chloroform. This ratio varies between about 2.2 and about 2.9, with an average of about 2.5. The lowest S:Co ratio observed here, 2.2, exceeds what would be expected if the sulfided components are present only as $MoS_2$ and $CoS_2$. Furthermore, the sulfur-to-cobalt ratio is significantly higher than what would be expected if cobalt is present as CoS and/or $Co_3S_4$.

Example 4

Evolution of Co:S Molar Ratios During Alcohol Synthesis

In this example, a Co—Mo—S powder with Mo:Co=2 (mole basis) and S:Co=2.1 (assuming Mo is present as $MoS_2$) is provided. This powder is compounded with $K_2CO_3$ such that Co:K=1 (mole basis), mixed with a binder, and formed into catalyst pellets. These pellets are loaded into reactors and operated under alcohol-synthesis conditions for varying periods of time as follows: sample A at 90 hours; sample B at 200 hours; and sample C at 500 hours. The pellets are then discharged under inert conditions and subjected to chemical analysis. Note that the three different samples herein are run in different reactors.

Catalyst sample A has a S:Co ratio of about 1.4 (assuming that Mo occurs as $MoS_2$), and 40-46% of the cobalt leaches into 3N HCl solution. Sample B has a S:Co ratio of about 0.5, and 50% of the cobalt leaches into 3N HCl solution. Sample C has a S:Co ratio of about 0.9, and 39-42% of the cobalt is extracted into 3N HCl.

It is therefore observed that a substantial fraction (about 40-50%) of cobalt is extracted into 3HCl and the S:Co ratio varies from about 0.45 to 1.4 even though, initially, S:Co was about 2.1 and only a small portion (in the range of 0.5-7%) of cobalt leaches from the initial catalyst. By contrast, 10% of the Co in RF-1 catalyst (Example 1) extracts into 3N HCl and the S:Co ratio in RF-1 catalyst is about 1.1. A large fraction (35-55%) of Co in catalytically used RF-2 catalyst is extractable into 3N HCl, while only 10% of Co in RF-1 is extractable into 3N HCl.

Example 5

Bulk Chemical Properties of Co/Mo/S Catalysts After 3800 Hours of Operation

Chemical analysis of alkali-promoted Co/Mo/S catalysts recovered from a pilot reactor after about 3800 hr operation reveals substantial changes from fresh catalysts. Sulfur content is quite low. Compared with catalysts aged between 50-500 hr, cobalt is less leachable. Carbon levels are high. C:H ratios increase as one moves downbed. Cobalt carbides may occur throughout the bed while molybdenum carbides may occur in the middle and bottom of the bed.

Seven samples of catalyst pellets (two top-bed, two mid-bed, three bottom-bed) are analyzed for total C, H, Co, Mo, S, and K. In addition, 3N HCl leachable Co, Mo, and S are determined. As expected, Mo:Co is about 2 and does not vary across the bed. Similarly, K:Mo is about 0.58 and does not vary across the bed.

Sulfur content declines from the top to bottom of the bed while carbon content increases. Acid-leachable cobalt is relatively low and roughly constant throughout the bed. Hydrogen content is comparable in the middle and bottom of the bed and somewhat lower in concentration at the top. One can assume that hydrogen occurs as $CH_2$ and that excess carbon is associated with Co or Mo.

|  | $S/M_{tot}$ | Excess $C/M_{tot}$ | Acid leachable cobalt |
| --- | --- | --- | --- |
| Fresh | 1.98 ± 0.05 | <0 | 0.088 ± 0.005 |
| Top | 1.52 ± 0.02 | 0.06 ± 0.06 | 0.24 ± 0.02 |
| Middle | 1.16 ± 0.02 | 0.30 ± 0.02 | 0.30 ± 0.08 |
| Bottom | 1.00 ± 0.01 | 0.48 ± 0.05 | 0.22 ± 0.02 |

For the middle and bottom of the bed, there is insufficient sulfur for Mo to occur only as $MoS_2$. The excess carbon content suggests that metal carbides may occur.

The leachability of cobalt evolves with time on stream in an alcohol-synthesis reactor. In good Co/Mo/S powders, the fraction of leachable cobalt is small, presumably since Co occurs as $CoS_2$ which, presumably, does not leach into 3 molar HCl at 93° C. After short to moderate times (50-200 hr) on stream, the fraction of leachable cobalt rises to 30-50%. For longer times on stream the fraction of leachable cobalt decreases. Variable-temperature XRD experiments under syngas atmosphere reveal that crystalline $CoS_2$ rapidly reduces to crystalline $Co_9S_8$. It is expected that non-crystalline $CoS_2$ similarly reduces to CoS materials.

Assuming that leachable cobalt occurs as CoS, the amount of sulfur available to Mo can be determined. Assuming that sulfur combines with Mo to make $MoS_2$, and given leachable Co as CoS, there is sufficient sulfur for all the Mo at the top of the bed to occur as $MoS_2$, for 80% of the mid-bed and 70% of the bottom-bed Mo to occur as $MoS_2$. It follows that roughly 80% of the cobalt and up to 30% of the molybdenum do not occur as sulfides. The mole ratio of excess carbon to metal not occurring as a sulfide is up to 0.5 at the top of the bed, 0.8 at mid bed, and about 1.0 at the bottom of the bed. The majority of cobalt appears to occur as cobalt carbides throughout the bed while there is a gradient of putative molybdenum carbides from the top to the bottom of the bed. The presence of crystalline $Co_2C$ was confirmed by XRD analysis.

Example 6

Co/Mo/S Catalyst Deactivation in Absence of Sulfur Addition

After running in a pilot unit for over 4000 hrs in the substantial absence of $H_2S$, an alkali-promoted Co/Mo/S catalyst is unloaded under inert conditions and loaded into a laboratory reactor where it is subjected to sulfur-free syngas at 310° C. and separately at 325° C. It is observed at either temperature that catalyst activity declines, the selectivity to ethanol declines (by about 30-40%), and the selectivity to hydrocarbons increases.

Deactivation is associated with changes in composition and chemical properties. For example, the ratio of sulfur to total metals drops from about 2 in the fresh catalyst to about 1.3 in deactivated catalysts. Furthermore, a significant portion of detected carbon in the deactivated catalysts can be assigned to the cobalt and molybdenum present, as metal carbides. For example, crystalline $Co_2C$ is observed by XRD in deactivated catalysts.

Example 7

Bulk Chemical Properties of Co/Mo/S Catalysts in the Presence of Methanol, with and without $H_2S$ Two catalyst samples each from Run A and Run B are analyzed for total S, Co, Mo, C, H, K, 3N HCl-leachable S, Co, Mo, and K, carbonate carbon, and elemental sulfur.

In Run A, the catalyst is exposed to methanol for 72 out of 185 hours on stream; $H_2S$ is absent. In Run B, the catalyst is exposed to methanol for 226 out of 403 hours on stream; $H_2S$ is present (about 80 ppm). It is hypothesized that $H_2S$ co-feed can stabilize catalyst performance in the face of high amounts of methanol injection; this is verified in Run B. It is also hypothesized that sulfur loss is less pronounced given $H_2S$ co-feed.

S/(Co+Mo) is substantially lower in Run A discharge compared to Run B discharge. The values are 1.735 (Run B) and 1.65 (Run A); the probability that these values are equal is only 2.2%. Cobalt leaching results further support the hypothesis that the cobalt function is damaged first as the catalyst losses sulfur. Only 18.0% of cobalt leaches into 3N HCl from Run B while 31.5% leaches from Run A. The probability that these values are equal is 1.6%. Molybdenum leachability (1.6% in Run B discharge, 1.4% in Run A discharge) is similar.

Assuming that Mo occurs as $MoS_2$, the transition-metal sulfide compositions of the discharges are: $2MoS_2 \cdot CoS_{1.19}$ after Run B and $2MoS_2 \cdot CoS_{0.95}$ after Run A. The higher level of S/Co after Run B is consistent with persulfide playing a role in ethanol synthesis; about 20% of cobalt could be associated with $S_2^{2-}$.

Given the relatively highly sulfided nature of these compositions, it is unlikely that much transition-metal carbide occurs in these discharge materials. A substantially larger fraction of carbon occurs as carbonate in Run B discharge. About 18.4% of carbon in Run B discharge occurs as carbonate while in Run A, only about 12.3% of carbon occurs as carbonate. The probability that these values are equal is 2.3%.

These results from bulk chemical analysis support the contention that a capable sulfide reagent maintains sufficient sulfur inventory in the catalyst to enable relatively efficient ethanol synthesis. The fact that cobalt leachability increases while molybdenum does not in the absence of a sulfiding agent supports a hypothesis that the cobalt function is essential for ethanol formation. An interesting, unexpected difference between the two discharge samples is the higher fraction of carbon that occurs as carbonate carbon in the presence of a sulfiding agent.

Example 8

Accelerated Aging of a Sulfided Catalyst

A potassium-promoted Co—Mo—S catalyst with initial S/(Co+Mo)=2 is operated under 2:1 CO:$H_2$ at 325° C. for several hundred hours. During the first hundred hours, sulfur evolves from the catalyst due, in part, to reduction of some $CoS_2$ to CoS-type phases, such as $Co_9S_8$. After about 100 hours, the amount of sulfur present in condensed alcoholic product is about 20 µg/ml.

After about 400 hours on stream, methanol together with 2:1 $H_2$:CO syngas is admitted to the top of the reactor. The methanol and syngas mixture approach to methanol synthesis equilibrium is between 25% and 50% at the top of the reactor. The amount of sulfur present in condensed alcoholic product rises to about 160 µg/ml. The acceleration factor during this period of methanol injection is about 8.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the appended claims.

All publications, patents, and patent applications cited in this specification are herein incorporated by reference in their entirety as if each publication, patent, or patent application were specifically and individually put forth herein. Also, this application hereby incorporates by reference herein U.S. patent application Ser. No. 12/204,543, filed Sep. 4, 2008, whose assignee is the same as the assignee of this patent application.

Where methods and steps described above indicate certain events occurring in certain order, those of ordinary skill in the art will recognize that the ordering of certain steps may be modified and that such modifications are in accordance with the variations of the invention. Additionally, the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A method of accelerated aging of a sulfide catalyst for the conversion of syngas to alcohols, said method comprising:
    (a) providing a test reactor including a test catalyst containing sulfur;
    (b) flowing syngas into said test reactor at conditions effective to produce an alcohol; and
    (c) injecting a suitable aging accelerant into said test reactor, wherein said aging accelerant is capable of causing sulfur loss from said test catalyst at a rate that is faster than the rate in the absence of said aging accelerant, wherein said aging accelerant comprises methanol.

2. The method of claim 1, wherein said methanol is injected in step (c) at about the equilibrium amount in accordance with a methanol/syngas reaction equilibrium produced under said conditions in step (b).

3. The method of claim 1, wherein said method is conducted for a test time selected from about 1 hour to about 200 hours.

4. The method of claim 3, wherein said test time is selected from about 10 hours to about 100 hours.

5. The method of claim 1, comprising an acceleration factor of at least 5, wherein said acceleration factor is the rate of sulfur loss from said test catalyst in the presence of said aging accelerant divided by the rate of sulfur loss in the absence of said aging accelerant.

6. The method of claim 5, wherein said acceleration factor is at least 10.

7. The method of claim 6, wherein said acceleration factor is at least 20.

8. The method of claim 1, further comprising measuring at least one parameter of interest at a plurality of times during operation of said test reactor, to generate a test response.

9. The method of claim 8, wherein said at least one parameter of interest is selected from the group consisting of CO conversion, ethanol selectivity, total alcohol selectivity, total alcohol productivity, methane selectivity, and sulfur concentration exiting said test reactor.

10. The method of claim 9, wherein said test response includes at least one correlation selected from the group consisting of decreasing CO conversion, decreasing ethanol selectivity, decreasing total alcohol selectivity, decreasing total alcohol productivity, increasing methane selectivity, and increasing sulfur concentration exiting said test reactor.

11. The method of claim 10, further comprising characterizing said test catalyst by predicting the lifetime or stability of a commercial catalyst with substantially the same composition as said test catalyst.

12. A method of characterizing a plurality of sulfide catalysts, wherein each catalyst composition is a distinct catalyst that is independently subjected to the following steps:
(a) providing a test reactor suitable for evaluating each of the sulfided catalysts;
(b) flowing syngas into the test reactor at conditions effective to produce an alcohol, for each of the sulfided catalysts; and
(c) injecting a suitable aging accelerant into the test reactor, for each of the sulfided catalysts, wherein the aging accelerant is capable of causing sulfur loss from each of the sulfided catalysts at a rate that is faster than the rate in the absence of the aging accelerant,
wherein said aging accelerant comprises methanol.

13. A method of characterizing performance of a sulfide catalyst for the conversion of syngas to alcohols under a plurality of process conditions, the method comprising:
(a) providing a test reactor suitable for evaluating the sulfided catalyst;
(b) flowing syngas into the test reactor at conditions effective to produce an alcohol, for each of the plurality of process conditions; and
(c) injecting a suitable aging accelerant into the test reactor, for each of the plurality of process conditions, wherein the aging accelerant is capable of causing sulfur loss from each of the sulfided catalysts at a rate that is faster than the rate in the absence of the aging accelerant,
wherein said aging accelerant comprises methanol.

* * * * *